(12) United States Patent
Lane et al.

(10) Patent No.: US 7,507,965 B2
(45) Date of Patent: Mar. 24, 2009

(54) SMART THERMAL IMAGING AND INSPECTION DEVICE FOR WHEELS AND COMPONENTS THEREOF AND METHOD

(75) Inventors: T Randall Lane, Lebanon, OH (US); Jerry Schlagheck, West Chester, OH (US)

(73) Assignee: Spirit Solutions, Inc, Dayton, OH (US)

( * ) Notice: Subject to any disclaimer, the term of this patent is extended or adjusted under 35 U.S.C. 154(b) by 341 days.

(21) Appl. No.: 11/307,601

(22) Filed: Feb. 14, 2006

(65) Prior Publication Data

US 2006/0180760 A1 Aug. 17, 2006

Related U.S. Application Data

(60) Provisional application No. 60/653,850, filed on Feb. 14, 2005.

(51) Int. Cl.
*G01J 5/02* (2006.01)

(52) U.S. Cl. .................................. 250/339.05

(58) Field of Classification Search ............ 250/339.4, 250/339.5, 338.1, 339.04, 339.05, 339.14, 250/340, 342; 246/169 R, 169 A, 169 D; 382/181

See application file for complete search history.

(56) References Cited

U.S. PATENT DOCUMENTS

| | | | | |
|---|---|---|---|---|
| 3,994,458 A * | 11/1976 | Winters | ................... | 246/169 A |
| 4,313,583 A * | 2/1982 | Bambara et al. | ........ | 246/169 A |
| 4,316,175 A * | 2/1982 | Korber et al. | ........... | 246/169 A |
| 4,501,006 A * | 2/1985 | Korenberg | ................... | 377/45 |
| 4,878,116 A | 10/1989 | Thomas et al. | | |
| 4,878,761 A | 11/1989 | Duhrkoop | | |
| 5,118,943 A * | 6/1992 | Le Bars et al. | ............... | 250/332 |
| 5,149,025 A * | 9/1992 | Utterback et al. | ........ | 246/169 A |
| 5,201,483 A | 4/1993 | Sutnar et al. | | |
| 5,381,700 A * | 1/1995 | Grosskopf, Jr. | ............ | 73/865.9 |
| 5,446,452 A * | 8/1995 | Litton | ................... | 340/870.17 |
| 5,448,072 A * | 9/1995 | Gallagher | .................... | 250/349 |
| 5,478,151 A | 12/1995 | Duhrkoop | | |
| 5,677,533 A * | 10/1997 | Yaktine et al. | ............... | 250/342 |
| 6,476,391 B1 * | 11/2002 | Zhang | ........................ | 250/330 |
| 6,476,722 B1 * | 11/2002 | Bidone | ........................ | 340/584 |
| 6,759,659 B2 | 7/2004 | Thomas et al. | | |
| 6,837,617 B1 * | 1/2005 | Koltunov et al. | ............ | 374/121 |
| 6,872,945 B2 * | 3/2005 | Bartonek | ............... | 250/339.04 |
| 7,298,869 B1 * | 11/2007 | Abernathy | ................... | 382/108 |
| 2002/0159770 A1 * | 10/2002 | Moultrie | ..................... | 396/265 |
| 2004/0005086 A1 * | 1/2004 | Wolff et al. | ................. | 382/118 |
| 2004/0164235 A1 * | 8/2004 | Miller | ........................ | 250/265 |
| 2004/0223062 A1 * | 11/2004 | Pettegrew et al. | ........ | 348/211.4 |
| 2006/0146377 A1 * | 7/2006 | Marshall et al. | ............. | 358/486 |
| 2006/0177104 A1 * | 8/2006 | Prokoski | ..................... | 382/108 |
| 2007/0152153 A1 * | 7/2007 | Bevan et al. | ............. | 250/338.1 |

FOREIGN PATENT DOCUMENTS

JP 08154193 A * 6/1996
WO WO 2004079659 A1 * 9/2004

* cited by examiner

*Primary Examiner*—David P Porta
*Assistant Examiner*—David S Baker
(74) *Attorney, Agent, or Firm*—R. William Graham

(57) ABSTRACT

A smart thermal imaging and inspection of wheels for the automatic inspection and analysis of railroad car wheels but can also be used for wheeled object that contain a bearing. The inventive device includes a thermal imaging camera, visual imaging camera, imaging processing unit. Users interface which allows for all parameters to be set.

32 Claims, 2 Drawing Sheets

SMART THERMAL IMAGING AND INSPECTION DEVICE FOR WHEELS AND COMPONENTS THEREOF AND METHOD

This application claims the benefit of provisional application U.S. 60/653,850 filed Feb. 14, 2005.

BACKGROUND OF THE INVENTION

1. Field of the Invention

The present invention relates generally to railroad Hotboxes and more specifically it relates to a smart thermal imaging and inspection device for wheels and components thereof for the automatic inspection and analysis of railroad car wheels or other wheeled vehicles.

2. Description of the Related Art

It can be appreciated that various forms of thermal imaging have been in use for years reading the temperature of wheels. A technology termed the Hotbox is the most common device and is found on railroads and uses infrared temperature measurements.

One type of system for measuring impermissible temperature increases of railway rolling stock wheels that are running hot includes an infrared temperature receiver which is usually located close to the rails so that an active window that subtends an angle to the normal can detect the bearings of a moving railroad car. A short period of time is available for temperature measurement, particularly at higher speeds.

The detection of the hottest point of an axle or a bearing can obscured or difficult to read in some instances. Wide scanning beams transverse to the longitudinal direction of the rail with an integrated signal have been used to some success. However, the integration that is provided by the detection of a relatively wide area in the longitudinal direction of the axles leads overall to a relatively small difference of the signals that are measured, so that reliable analysis is not possible without some difficulty. In the case of relatively complete bearing covers, impermissible heating can only be detected over a small part of the axial length of an axle since, by comparison, the other areas are significantly cooler. Some systems propose using rotating and oscillating mirrors to overcome such problems in the art.

One problem with the conventional Hotbox is that it employs a single pyrometer to determine temperature. Another problem with conventional Hotbox technology is the viewing window can easily become blocked due to leaves and other objects blocking the view due in part to the fact the Hotbox faces towards the sky. Another problem with conventional Hotbox technology is that weather conditions can block the field of view. The fundamental problem when using Hotbox or similar infrared technologies is that emissivity (the ability of a surface to emit radiation, measured as the ratio of the energy radiated by a surface to that radiated by a black body at the same temperature) correction is overlooked and actual temperature measurements can be in error by greater than twenty percent.

In addition, commercial vehicles, such as trucks, are involved in hundreds of thousands of crashes, resulting in thousands of fatalities each year. In many cases, defective brakes or tires are a factor in these crashes. Infrared brake screening technology has been employed to help identify maintenance needs before these deficiencies create problems on the road, such as a system which screens for brake defects and produces results in seconds. In one system, as a commercial vehicle decelerates to enter a roadside inspection facility, the system scans the vehicle's wheels with an infrared camera. The screen displays thermal images of the wheels, showing their relative temperatures. Because the application of brakes creates heat, the wheels with functional (warm) brakes appear bright white in the infrared image, while the wheels with inoperative (cold) brakes appear dark. The color image helps the operator easily identify a vehicle with functional or inoperative brakes.

Again, significant problems with conventional Hotbox technology include a single spot pyrometer used to determine temperature of a wheel that is three feet in diameter and that the viewing window easily become blocked by leaves, weather conditions can and other objects.

The present invention provides a smart thermal imaging and inspection for wheels and components thereof which substantially departs from the conventional concepts and designs of the prior art and improves upon the art by providing for the automatic inspection and analysis of railroad car wheels or for wheeled objects such as semi-trucks at weigh stations, sub-way cars or any wheeled device that has a bearing subject to such problems.

SUMMARY OF THE INVENTION

An object of the present invention is to provide a smart thermal imaging and inspection device for wheels and components thereof that will overcome the shortcomings of the prior art devices.

Another object of the present invention is to provide a smart thermal imaging and inspection device for wheels and components thereof for the automatic inspection of wheeled objects containing a bearing, such as railroad car wheels and truck wheels.

Still another object is to provide a smart thermal imaging and inspection device for wheels and components thereof that provides for automatic real time detection and analysis of wheels and components thereof.

A further object is to provide for single time frame analysis of wheels and components thereof.

Accordingly, the present invention provides a new smart thermal imaging and inspection device for wheels and components thereof wherein the same can be utilized for the automatic inspection and analysis of railroad car wheels and other wheeled object containing a bearing. The device includes a thermal imaging camera, imaging processing unit and input/output relay assembly. The device captures a 2D array of thermal data for mathematical processing, wherein the imaging processing unit performs an analysis of the acquired 2D array of thermal data. The device provides a user interface which allows for selection of parameters to be set, such as camera shutter speed and line scan, etc. There is also provided a visual imaging camera which provides image data to the processor in order to correct emissivity readings. The present invention provides real time and automatic inspection device for wheels and components thereof, such as hot wheels, hot bearings and slide wheels or any combination of thereof. The image processing unit also provides for rotational stress (fatigue/fracture) analysis or tire delamination in the case of tractor trailers with its 2D array post processing analysis of the thermal images acquired by the image processing software.

More particularly, there is provided a smart thermal imaging and inspection device for wheel, which includes an infrared camera located adjacent to the wheel, wherein the infrared camera is positioned to have field of view which is traversed by the wheel to enable capturing infrared spectrum image data corresponding to emissivity, a visual camera located adjacent to the wheel, wherein the visual camera is positioned to have field of view which is traversed by the wheel to enable capturing visible spectrum image data, a computer based device having an image processor operably connected to each the camera for receiving the infrared spectrum image data and the visible spectrum image data, the image processor operably associated with memory and software for storing the image data, analyzing the image data and generating a signal indicative of a condition of the wheel. The software employs the visible spectrum image data to correct emissivity readings as well as uses the captured infrared spectrum image data for use in determining infrared curvature correction, thermal analysis, image noise removal, and rotational motion analysis of said spectrum image data.

A method of inspecting an object is provided. The method includes the steps of: employing an infrared camera adjacent to the object, wherein the infrared camera is positioned to have field of view which is traversed by the object to enable capturing infrared spectrum image data corresponding to emissivity; employing a visual camera located adjacent to the object, wherein the visual camera is positioned to have field of view which is traversed by the object to enable capturing visible spectrum image data; employing a computer based device having an image processor operably connected to each the camera for receiving the infrared spectrum image data and the visible spectrum image data, the image processor operably associated with memory and software for storing the image data; and analyzing the image data and generating a signal indicative of one of a normal and abnormal condition of the object.

There has thus been outlined, rather broadly, the more important features of the invention in order that the detailed description thereof may be better understood, and in order that the present contribution to the art may be better appreciated. There are additional features of the invention that will be described hereinafter. In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

Other objects and advantages of the present invention will become obvious to the reader and it is intended that these objects and advantages are within the scope of the present invention. To the accomplishment of the above and related objects, this invention may be embodied in the form illustrated in the accompanying illustrations, attention being called to the fact, however, that the illustrations are descriptive only, and that changes may be made in the specific construction illustrated.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DETAILED DESCRIPTION OF THE INVENTION

Figure 1:
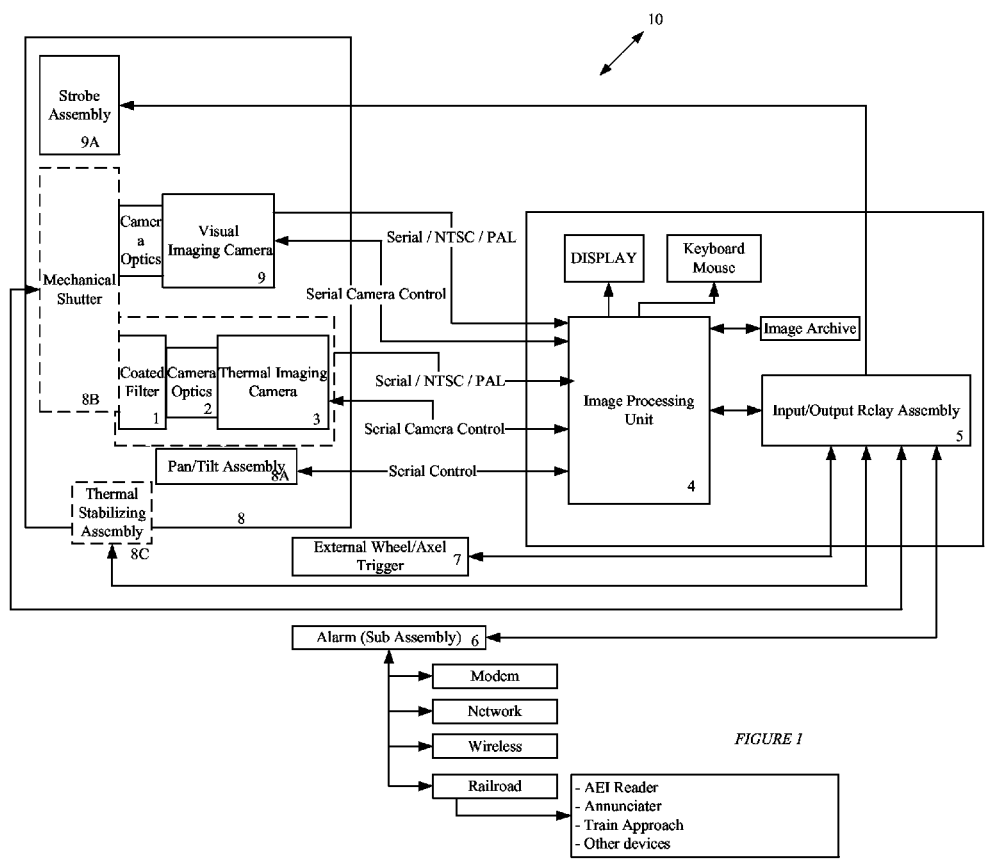
FIG. 1 is a block diagram of the present invention.

Turning now to the drawings, in which similar reference characters denote similar elements throughout the several views, the attached illustrations show a smart thermal imaging and inspection (hereinafter referred to as "STII") device for wheels and components thereof which is generally designated by the numeral 10. The STII device 10 includes a thermal imaging camera 3, and imaging processing unit 4 and input/output relay assembly 5.

The thermal imaging camera 3 is comprised of a 2D focal plane array, camera optics 2, and coated filter 1, wherein the thermal imaging camera 3 is sensitive in the 8 to 14 micron range. The STII device 10 can utilize either an electronic or a spectral optical coated band pass filter to focus on specific wavelengths, such as molten steel that is in the region of 2 to 3 microns to generate thermal data to be normalized and/or analyzed. By employing the thermal imaging camera 3 and associated camera optics 2 and coated filter 1, a range of 1 to 14 microns can be normalized and analyzed.

The image processing unit 4 is used to perform the analysis of the generated thermal data. The image processing unit 4 includes a computer having suitable memory, processor board, operating software operably disposed thereon, a keyboard, mouse and display operably associated therewith. Thermal imaging software, is operably disposed on the thermal processing unit 4, for capturing and storing thermal data generated by the thermal imaging unit 3 in an image archive of the memory and applying specific algorithms, such as neural net technology or pattern recognition software, and determining if an anomaly or "concerning" condition exists. The image processing unit 4 can be part of a large scale integrations (LSI) or installed in a general computer running Windows, UNIX or other operating system.

Figure 3:
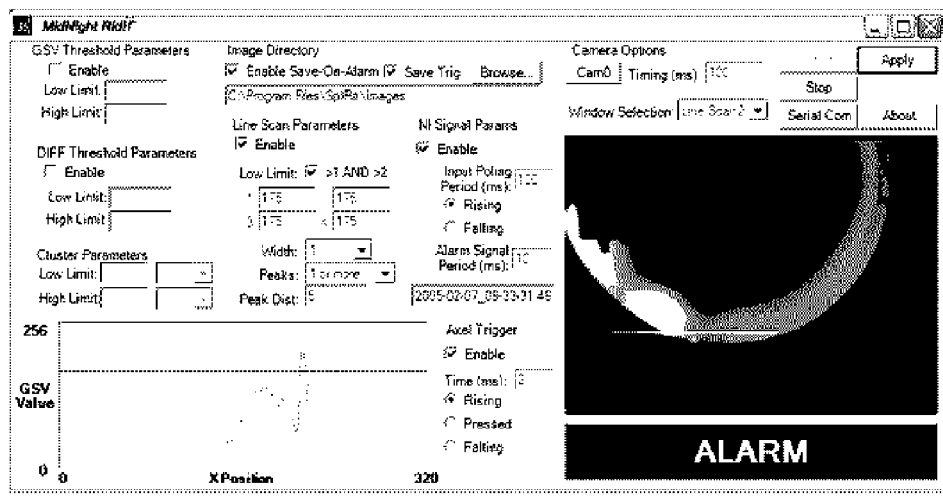
FIG. 3 is a graphic user interface of the present invention.

Additionally, the thermal processing software provides a graphical user interface as seen in FIG. 3 which provides for various operating parameters to be easily set by an operator. Such parameters include: Gray Scale Value (GVS) Threshold Parameters which can be enabled/disabled and when enabled set to between a low and high limit value; Differential (DIFF) Threshold Parameters (A threshold Parameter is associated with an upper and lower control) which can be enabled/disabled and when enabled set to between a low and high limit value; Cluster Parameters which can be enabled/disabled and when enabled set to between a low and high limit value for an area that is a fraction of the full 2D array; Line Scan Parameters which can be enabled/disabled and when enabled set to between a low and high limit value; width, number of peaks and peak distance; Signal Parameters (Signal parameters are associated to the various I/O signals—such a train approach, axle trigger) which can be enabled/disabled and when enabled permits input polling period with an indication of rising or falling and alarm signal period value; Camera Options including timing and window selection; Axel Trigger (is an electromechnaical or optical switch that senses an event, i.e., the wheel/axel trigger (7)) which can be enabled/disabled and when enabled set to a time (millisecond) and select whether rising, pressed or falling. The user can easily define such parameters to perform the automatic inspection. The graphical user interface can be easily modified for use to fit the particular wheels or object being inspected. Also, the graphical user interface can provide windows which illustrate both visually and graphically the thermal data which has been analyzed and provide an indication of condition, i.e., normal or suspect" and generate an "Alarm" signal indicative of such suspect condition.

The thermal imaging camera (3), optics (2) and filter (1) are connected to the imaging processing unit (4) via a NTSC (National Television Standards Committee is a standard used in North America and Japan; it has the ability to display up to 525 lines of resolution) PAL (Phase Alternating Line) or high frame rate serial protocol. The image processing unit 4 is operably connected to an input/output relay assembly (5) to provide the necessary signals to send or receive events such as "object approaching," "time to inspect" and "alarm functions". In this regard, input/output relay assembly (5) is operably connected to an alarm (sub assembly) (6) which is operably connected via a modem, network, wireless connection to a railroad, wherein the railroad can include an (AEI) Reader (Automatic Equipment Identification or AEI is technology that uses electronically coded tags to identify railcars, locomotives, Intermodal vehicles and end of train devices. These tags are placed on both sides of the cars and are encoded with the owner's code and number, length, equipment group code, tag type, car/locomotive number, side indicator code (left or right), number of axles, bearing type code and platform identifier code (rail car tag). An RF module transmits an unmodulated signal to the tag passing by and in turn the tag reflects a modulated signal back. The RF module transfers the information to a reader and the reader decodes the information that is used by the railroads. The tags are read without error or duplication at high speeds as the trains pass by the AEI locations), an annunciator which can be an audible and visual signaling device, train approach or other devices as known in the art.

The input/output relay assembly (5) is also operably connected to an external wheel/axel trigger (7) which is also operably connected therethrough to the image processing unit 4. Additionally, the input/output relay assembly (5) is operatively connected to a pan/tilt assembly (8A), mechanical shutter (8B), and a thermal stabilizing assembly (8C), which can be an HVAC unit. Further, the input/output relay assembly (5) is operatively connected to a strobe assembly (9A) whereupon receiving a signal from the external wheel trigger (7), the imaging processing unit (4) via the input/output relay assembly (5) initiates the strobe assembly (9A), mechanical shutter (8B) in an appropriate sequence. Visual imaging camera and optics (9) are also provided and are operably connected to the imaging processing unit (4) via a NTSC, PAL and high frame rate serial protocol (serial camera control) and are controlled thereby. The components of the device are mounted in a climatic enclosure (8) to provide protection from environmental conditions and the camera(s) are mounted via a pan and tilt assembly (8A) for aiming the camera(s) at the desired object and can be adjusted through the graphics user interface. Other variations based on the inspection type can utilize a visual or thermal imaging camera.

The coated filter (1), which can be a spectral band pass optical filter, is integrated within the thermal imaging camera (3). The coated filter (1) provides a narrow and wide band transmission for the detection of various conditions. The filter pass is 1 to 5 micron wavelength for the detection of a slide wheel and passes 5 to 14 microns for other conditions such as a hot wheel and hot bearing. The thermal imaging processing unit (4) applies another algorithm in real time to assist in the inspection of the wheels of the railroad car.

Figure 2:
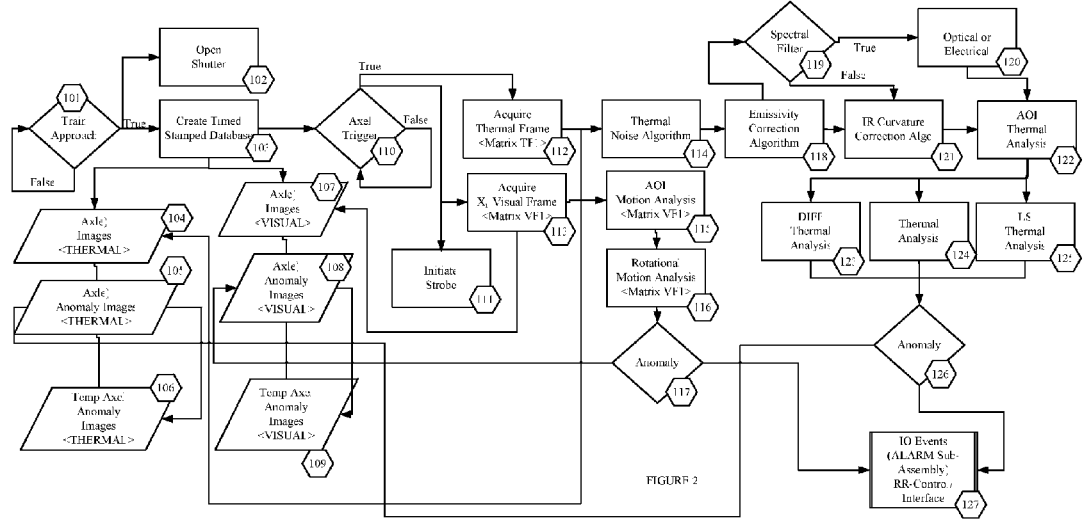
FIG. 2 is a flow chart diagram illustrating an operation of the invention.

Operation: The image processing analysis method takes place as follows wherein the STII device 10 is initiated upon receiving a "true" signal by sensing voltage changes on input/output relay assembly (5), wherein the STII device 10 performs a sequence of mechanical, digital and mathematical operations. As illustrated in FIG. 2, as a train approaches (step 101), upon receiving a true signal indicating train is approaching, a mechanical shutter (8B) is opened (step 102) allowing the infrared imaging camera (3) and/or a visual imaging camera (9) to view an area. The mechanical shutter (8B) is part of the climatic enclosure (8) that protects the items from various environmental conditions when not active.

Concurrently the image processing unit (4) (illustration 1) creates and appends records (spectrum image data) to the memory in a main database management system with folders that are all time stamped (step 103) for triggered images, i.e., each image data captured, including temporary anomaly image data and anomaly image data, i.e., any of the captured image data which are suspect, and associated image data folders for either the infrared imaging camera (3) and/or visual imaging camera (9) (steps 104-109).

Thus, when the train (or vehicle) passes by the STII device 10, the wheel trigger (7) senses (step 110) the train via a electromechanical or optical device and the strobe assembly 9A is illuminated (step 111) to emit towards the STII device 10 at a frequency sufficient to freeze (enable a still snap shot) area of interest motion for a period of typically 60 ms. Strobe duration and frequency is base on the speed of the unit passing the camera(s).

Additionally, a numerical 2D matrix (step 112) is acquired from the thermal imaging camera (3) and stored. The image area of interest is analyzed for material differences (step 114) such a mud or other foreign particles by means of a thermal gradient finite element analysis wherein a step function indicates an anomaly exits in material. Any particles identified as be inconsistent with a thermal conductivity transfer function in normalized by a nearest neighbor algorithm and pixel X is corrected to the material under analysis.

A numerical 2D matrix (step 113) is acquired from the visual camera 9 and a sequential numerical 2D matrix (step 115) is acquired from the visual camera 9. Movement algorithms and pattern recognition determines if the acquired/captured image of the wheel is rotating. The visual image data is stored for later image fusion, e.g., combining the infrared image data and visual image data together in a fusion manner wherein structural components of the visual image data are applied to thermal data.

Based on thermal conductivity, temperature of the material emissivity is corrected to the 2D matrix (step 118). Concurrently the data is analyzed with the benefit of optical coated filter (1) that is attached to the optics (2) of the lens and provides for a dual band analysis for emissivity correction and validation (step 119). If a "true" reading exists, then using calibration lookup tables known in the art for lens abrasions and other optical anomalies, the corrections are applied to the 2D matrix (step 120). If false, a curvature algorithm is applied to the 2D matrix to fix the plane of view normal to the object/area of interest into a flat plane view (step 121). Assuming the path through (step 120) is complete, (step 122) Automated Optical Inspection (AOI) thermal analysis is performed through this algorithm which employs lookup tables derived from empirical data studies derived from an analysis of steel or rubber, in the instant case for example, and expected decibel (db) power losses of varying angles of thermal radiation. All thermal data is numerically combined to represent a flat object (step 122).

This data (step 122) is analyzed with a differential algorithm that determines if the area of interest meets between both upper and lower control limits (step 123). The data (step 122) is processed using thermal analysis pattern recognition (step 124) in the thermal domain for unique patterns that identify such anomalies as delamination, brakes dragging, bearing and similar anomalies associated to wheeled objects. The data (step 122) is analyzed using thermal line scan (LS) (step 125) methodologies that are used to provide mechanical spatial data and pattern recognition. Data produced from the line scan algorithm is passed to step 123 and step 124 for further object alignments.

Data from step 116 can be fused with data step 120. The visual data combined with the thermal data provides for a more robust analysis by understanding the material characteristics and the associated radiation in the thermal domain. Depending on the analysis approached utilized, thermal, visual or fused or any combination, if any parameters fall outside the upper or lower control limits and alarm is generated (step 117 and/or step 126). The exchange of the alarm signals, such as Railroad (RR) control interface (step 127) is made through a serial communication port for data input/output to other devices and the section provides for input from external equipment such as label reading, RFID information and similar media types.

The present invention thus provides a device or system designed to assist with inspection of railroad wheels as they pass through the inspection area. Using a thermal imaging camera source combined with visual imaging processing technologies the system can determine if a condition is present for slide wheel, hot bearing and hot wheel. The system acquires data and then performs the smart inspection in real time. The device captures a 2D array of thermal data for mathematical processing, wherein the imaging processing unit performs an analysis of the acquired 2D array of thermal data. The device provides a user interface which allows for selection of parameters to be set, such as camera shutter speed and line scan, etc. There is also provided a visual camera which provides image data to the processor in order to correct emissivity readings. The present invention provides real time and automatic inspection device for wheels and components thereof, such as hot wheels, hot bearings and slide wheels or any combination of thereof. The image processing unit also provides for rotational stress (fatigue/fracture) analysis or tire delamination in the case of tractor trailers with its 2D array post processing analysis of the thermal images acquired by the image processing software.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention. The term "wheel" as set forth in the claims is intended to cover a wheel and/or components thereof.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention. With respect to the appended claims, it will be apparent that modifications, derivations and improvements will be within the scope of claims.

What is claimed is:

1. A smart thermal imaging and inspection device for a wheel, which comprises:

an infrared camera located adjacent to the wheel, wherein said infrared camera is positioned to have field of view which is traversed by the wheel to enable capturing infrared spectrum image data corresponding to emissivity;

a visual camera located adjacent to the wheel, wherein said visual camera is positioned to have field of view which is traversed by the wheel to enable capturing visible spectrum image data; and a computer based device having an image processor operably connected to each said camera for receiving said infrared spectrum image data and said visible spectrum image data, said image processor operably associated with memory and software for storing said image data, and pattern recognition software for analyzing said image data and generating a signal indicative of one of a normal and abnormal condition of the wheel and thereby enable emissivity correction.

2. The smart thermal imaging and inspection device for wheel of claim 1, wherein said software employs said visible spectrum image data to correct emissivity.

3. The smart thermal imaging and inspection device for wheel of claim 1, wherein said software employs said infrared spectrum image data to correct emissivity.

4. The smart thermal imaging and inspection device for wheel of claim 1, wherein said cameras are operably disposed within a housing which includes a controllably openable shutter interposed between said cameras and said fields of view and which is operably connected to said computer based device in a manner to enable control of said shutter.

5. The smart thermal imaging and inspection device for wheel of claim 4, which includes a thermal stabilizing assembly operably connected to said mechanical shutter and said computer based device.

6. The smart thermal imaging and inspection device for wheel of claim 4, which includes an input/output relay which is operably interposed between said mechanical shutter and said computer based device and a wheel trigger which is operably connected to said input/output relay in a manner to send a signal to said input/output relay, wherein upon receiving said signal said input/output relay assembly sends a signal to actuate said shutter.

7. The smart thermal imaging and inspection device for wheel of claim 1, which includes a controllably illuminable strobe light disposed in a manner to illuminate an area within said fields of view and which is operably connected to said computer based device in a manner to enable control of said strobe.

8. The smart thermal imaging and inspection device for wheel of claim 7, which includes an input/output relay which is operably interposed between said strobe and said computer based device and includes a wheel trigger which is operably connected to said input/output relay in a manner to send a signal to said input/output relay, wherein upon receiving said signal said input/output relay assembly sends a signal to actuate said strobe.

9. The smart thermal imaging and inspection device for wheel of claim 1, which includes a wheel trigger which is operably connected to said computer based device in a manner to send a signal to said computer based device, wherein upon receiving said signal said image processor activates said cameras to capture said spectrum image data.

10. The smart thermal imaging and inspection device for wheel of claim 1, which includes a pan tilt assembly operably connected to said computer based device.

11. The smart thermal imaging and inspection device for wheel of claim 1, wherein said image processor has operably associated graphic user interface software which enables at least one of infrared curvature correction, emissivity correction, thermal analysis, image noise removal, and rotational motion analysis of said spectrum image data.

12. A smart thermal imaging and inspection device for an object, which comprises: an infrared camera located adjacent to the object, wherein said infrared camera is positioned to have field of view which is traversed by the object to enable capturing infrared spectrum image data corresponding to emissivity; a visual camera located adjacent to the object, wherein said visual camera is positioned to have field of view which is traversed by the object to enable capturing visible spectrum image data; and a computer based device having an image processor operably connected to each said camera for receiving said infrared spectrum image data and said visible spectrum image data, said image processor operably associated with memory and software for storing said image data, and pattern recognition software analyzing said image data and generating a signal indicative of one of a normal and abnormal condition of the object and thereby enable emissivity correction.

13. The smart thermal imaging and inspection device for the object of claim 12, wherein said software employs said visible spectrum image data to correct emissivity.

14. The smart thermal imaging and inspection device for the object of claim 12, wherein said software employs said infrared spectrum image data to correct emissivity.

15. The smart thermal imaging and inspection device for the object of claim 12, wherein said cameras are operably disposed within a housing which includes a controllably openable shutter interposed between said cameras and said fields of view and which is operably connected to said computer based device in a manner to enable control of said shutter.

16. The smart thermal imaging and inspection device for the object of claim 15, which includes a thermal stabilizing assembly operably connected to said mechanical shutter and said computer based device.

17. The smart thermal imaging and inspection device for the object of claim 15, which includes an input/output relay which is operably interposed between said mechanical shutter and said computer based device and an object trigger which is operably connected to said input/output relay in a manner to send a signal to said input/output relay, wherein upon receiving said signal said input/output relay assembly sends a signal to actuate said shutter.

18. The smart thermal imaging and inspection device for object of claim 15, which includes a thermal stabilizing assembly operably connected to said mechanical shutter and said computer based device.

19. The smart thermal imaging and inspection device for the object of claim 12, which includes a controllably illuminable strobe light disposed in a manner to illuminate an area within said fields of view and which is operably connected to said computer based device in a manner to enable control of said strobe.

20. The smart thermal imaging and inspection device for the object of claim 19, which includes an input/output relay which is operably interposed between said strobe and said computer based device and includes a object trigger which is operably connected to said input/output relay in a manner to send a signal to said input/output relay, wherein upon receiving said signal said input/output relay assembly sends a signal to actuate said strobe.

21. The smart thermal imaging and inspection device for the object of claim 12, which includes a trigger to indicate when the object is in said field of view which is operably connected to said computer based device in a manner to send a signal to said computer based device, wherein upon receiving said signal said image processor activates said cameras to capture said spectrum image data.

22. The smart thermal imaging and inspection device for the object of claim 12, which includes a pan tilt assembly operably connected to said computer based device.

23. The smart thermal imaging and inspection device for the object of claim 12, wherein said image processor has operably associated graphic user interface software which enables at least one of infrared curvature correction, emissivity correction, thermal analysis, image noise removal, and rotational motion analysis of said spectrum image data.

24. A method of inspecting an object, which comprises the steps of: employing an infrared camera adjacent to the object, wherein said infrared camera is positioned to have field of view which is traversed by the object to enable capturing infrared spectrum image data corresponding to emissivity; employing a visual camera located adjacent to the object, wherein said visual camera is positioned to have field of view which is traversed by the object to enable capturing visible spectrum image data; employing a computer based device having an image processor operably connected to each said camera for receiving said infrared spectrum image data and said visible spectrum image data, said image processor operably associated with memory and software for storing said image data; and pattern recognition software analyzing said image data and generating a signal indicative of one of a normal and abnormal condition of the object and thereby enable emissivity correction.

25. The method claim 24, wherein said software employs said visible spectrum image data to correct emissivity.

26. The method claim 24, wherein said software employs said infrared spectrum image data to correct emissivity.

27. The method claim 24, wherein said cameras are operably disposed within a housing which includes a controllably openable shutter interposed between said cameras and said fields of view and which is operably connected to said computer based device in a manner to enable control of said shutter.

28. The method claim 24, which includes employing a controllably illuminable strobe light disposed in a manner to illuminate an area within said fields of view and which is operably connected to said computer based device in a manner to enable control of said strobe.

29. The method claim 24, which includes employing a trigger to indicated when the object is in view and which is operably connected to said computer based device in a manner to send a signal to said computer based device, wherein upon receiving said signal said image processor activates said cameras to capture said spectrum image data.

30. The method claim 28, which includes employing an input/output relay which is operably interposed between said strobe and said computer based device and includes a object trigger which is operably connected to said input/output relay in a manner to send a signal to said input/output relay, wherein upon receiving said signal said input/output relay assembly sends a signal to actuate said strobe.

31. The method claim 24, which includes employing a pan tilt assembly operably connected to said computer based device.

32. The method claim 24, wherein said image processor has operably associated graphic user interface software which enables at least one of infrared curvature correction, emissivity correction, thermal analysis, image noise removal, and rotational motion analysis of said spectrum image data.

\* \* \* \* \*